United States Patent [19]

Schelm

[11] Patent Number: 4,716,034
[45] Date of Patent: Dec. 29, 1987

[54] PACKAGED DENTAL CREAM

[75] Inventor: Sandra L. Schelm, Highland Park, N.J.

[73] Assignee: Colgate-Palmolive Company, New York, N.Y.

[21] Appl. No.: 803,040

[22] Filed: Nov. 27, 1985

[51] Int. Cl.$^4$ ............................................. A61K 7/16
[52] U.S. Cl. ..................................... 424/49; 424/57
[58] Field of Search ............................ 424/49, 57, 835

[56] References Cited

U.S. PATENT DOCUMENTS

| | | | |
|---|---|---|---|
| 3,260,410 | 7/1966 | Drandt et al. | 222/107 |
| 4,418,841 | 12/1983 | Eckstein | 222/107 |
| 4,437,591 | 3/1984 | von Schuckmann | 222/391 |
| 4,528,182 | 7/1985 | Curtis et al. | 424/54 |
| 4,540,576 | 9/1985 | Zahradnik | 424/151 |
| 4,556,553 | 12/1985 | Suganuma et al. | 424/52 |

OTHER PUBLICATIONS

Lion Corp., JA 0213706 Abstract, Dec. 1983, Abst. No. C84-009213, Buccal Compsn. for Prevention of Dental Caries.

Primary Examiner—J. R. Brown
Assistant Examiner—F. T. Moezie
Attorney, Agent, or Firm—Robert L. Stone; Murray M. Crill; Herbert S. Sylvester

[57] ABSTRACT

Dental cream in contact with a polyolefin resin surface of a package such as a laminate tube, a mechanical dispenser or a flexible sachet. The dental cream contains as at least the major portion of which is a dentally acceptable water-insoluble polishing material alpha-alumina trihydrate, a liquid vehicle and a gelling agent and an agent to reduce pH containing phosphate ion. The liquid vehicle contains water, glycerine and sorbitol and, as an additive to prevent syneresis due to contact between the dental cream and the polyolefin resin, polyethylene glycol of average molecular weight or about 200–1000.

12 Claims, No Drawings

PACKAGED DENTAL CREAM

This invention relates to a dental cream packaged in a plastic laminate tube, mechanical dispenser, flexible sachet or the like. In particular it relates to a dental cream in compatible contact with a polyolefin surface of a package such as a plastic laminate dental cream tube, mechanical dispenser or flexible sachet.

Dental creams have been packaged for many years in flexible metal tubes such as wax lined lead tubes, unlined aluminum tubes or aluminum tubes having an epoxy resin lacquer coating thereon. In recent years flexible form-retaining laminated plastic tubes have been increasingly used.

Plastic laminated dental cream tubes typically comprise an inner polyolefin resin layer which is in direct contact with the dental cream and at least one intermediate layer, including an aluminum foil layer which inhibits loss of flavor from the dental cream. Desirably, an intermediate paper layer which provides stiffness to the tube is also present. The outer layers are typically of polyolefin resins, one of which may be colored white and bears printed indicia with a clear polyolefin laminate overlay to protect the indicia. Additional intermediate laminate layers of flexible plastic may also be present.

Mechanical dental cream dispensers may also have a polyolefin surface in contact with dental cream contained therein. In fact, the polyolefin itself may be the housing of the dispenser. Flexible sachet packets may also have a polyolefin surface in contact with dental areas.

Dental creams typically contain a liquid vehicle of water and humectant, a gelling agent solid vehicle and a water-in-soluble dental polishing agent. Dental creams composed of such materials wherein the humectant comprises glycerine and sorbitol and the polishing material is at least in major part an alpha alumina trihydrate have been successfully packaged in flexible metal toothpaste containers including aluminum tubes having an internal coating of an epoxy resin lacquer layer. However, it is observed that when such dental creams are packaged in containers having an interior polyolefin surface such as plastic laminated dental cream tubes, mechanically operated dental cream dispensers or flexible sachets, that syneresis occurs and liquids separate from solids, rendering the dental cream undesirable, when the pH of the dental cream is reduced with a water-soluble material which provides phosphate ion.

It is an advantage of this invention that phase separation of a dental cream packaged in contact with a polyolefin material is substantially prevented. Other advantages will be apparent from consideration of the following disclosure.

In accordance with certain of its aspects, this invention relates to a packaged dental cream wherein said dental cream is in direct contact with a polyolefin resin surface, said dental cream comprising at least about 20% by weight of a liquid vehicle comprising water, glycerine, sorbitol and polyethylene glycol of average molecular weight of about 200–1000, the weight ratio of glycerine to sorbitol being from 0.25:1 to about 3:1 and the weight ratio of the total amount of glycerine and sorbitol to said polyethylene glycol being from about 60:1 to about 6:1, a solid vehicle comprising about 0.05%–10% by weight of gelling agent, about 20–75% by weight of a dentally acceptable water-soluble polishing material, at least a major portion of which is alpha-alumina trihydrate and a water-soluble material to reduce the pH of the dental cream to about 6–8 which provides phosphate ion.

In dental cream formulations, the liquids and solids are necessarily proportioned to form a creamy mass of desired consistency which is extrudible from its package. The liquids in the present dental cream comprise chiefly water, glycerine and sorbitol, together with a minor amount of polyethylene glycol of molecular weight of about 200–1000, preferably about 600–1000. The total liquid vehicle comprises at least about 20% by weight of the formulation. It is preferred to use also a gelling agent in dental creams such as the natural and synthetic gums and gumlike materials, e.g. carrageenans such as Irish moss, gum tragacanth, sodium carboxymethyl cellulose, hydroxyethyl cellulose, polyvinyl pyrrolidone, sodium alginate, guar gum, starch, xanthan and the like, including mixtures thereof. Irish Moss, sodium carboxymethyl cellulose and hydroxyethyl cellulose including mixtures thereof are compatible particularly and are preferred gelling agents. The gum content is usually in an amount about 0.05–10% and preferably about 0.5–5% by weight of the formulation.

Water is generally incorporated into the dental cream in amount of about 10–50% by weight, preferably about 15–35%. Glycerine and sorbitol together generally comprise abouf 15–50% by weight, preferably about 20–35% of the dental cream, with the weight ratio of glycerine to sorbitol being from about 0.25:1 to about 3:1, typically from about 0.25:1 to about 0.8:1 and preferably from about 0.6:1 to about 0.8:1. Amounts of sorbitol as used herein are of sorbitol syrup, as commercially available, that is 70% by weight sorbitol in 30% by weight of water.

Low molecular weight polyethylene glycol of average molecular weight of about 200–1000, preferably about 600–1000, disperses readily in the liquid vehicle and is effective to prevent the dental cream from undergoing syneresis when in direct contact with a polyolefin resin surface of a dental cream package. In order to effect dispersion readily, grades of polyethylene glycol which are normally solid at room temperature are heated to liquify them. The weight ratio of the total amount of glycerine and sorbitol to polyethylene glycol is from about 60:1 to about 6:1, preferably from about 15:1 to about 10:1. Typically, at least 0.5% by weight of polyethylene glycol is present, preferably about 0.5–5%.

Dentally acceptable water-insoluble polishing agent is present in the dental cream in amount of about 20–75% by weight, preferably about 35–60%. At least the major portion, that is, about 50–100% of the polishing material is alpha-alumina trihydrate. The minor portion of the polishing material, if present, typically comprises about 5–20% by weight of the polishing material, dicalcium, phosphate dihydrate, anhydrous dicalcium phosphate, calcium carbonate, tricalcium phosphate, calcium pyrophosphate, dimagnesium phosphate trihydrate, magnesium carbonate, calcined alumina, zirconium silicate and insoluble sodium metaphosphate.

Dentally acceptable water-insoluble alpha-alumina polishing agent is typically employed in small particle size, e.g. wherein at least about 85% of the particles are smaller than 20 microns and is preferably hydrated, such as that classified as gibbsite (alpha alumina trihydrate) and normally represented chemically as $Al_2O_3$3-

H₂O or Al(OH)₃. The average particle size of gibbsite is generally about 6 to 9 microns. However, larger particle size alpha-alumina trihydrate, e.g. wherein 20–70% of the particles exceed 20 microns in size, may also be used. A particularly desirable grade of alpha-alumina trihydrate, available from Alcoa as C-333 is a fine grade of gibbsite having the following size distribution:

| Microns | Percent |
|---------|---------|
| <30 | 94–99 |
| <20 | 85–93 |
| <10 | 56–67 |
| <5 | 28–40 |

Unless the pH of the dental cream is adjusted, dental cream containing a substantial amount of alpha-alumina trihydrate is generally highly alkaline, e.g. about 9–10.5. Accordingly acidic materials are often added to such dental creams in order to reduce the pH, typically to about 6 to 8. Water-soluble phosphate materials, particularly inorganic phosphate materials are effective to produce such reduction in alkalinity. Such materials include orthophosphates particularly orthophosphoric acid and alkali metal or ammonium monoacid orthophosphates or diacid orthophosphates. Sodium diacid orthophosphate and hydrates thereof are preferred. The amount of these materials is that sufficient to adjust the pH to about 6–8; e.g. sodium diacid orthophosphate (monohydrate or anhydrous) is typically present in amount of about 0.15–0.50% by weight. Such phosphate pH adjusting materials render the dental creams subject to syneresis when in contact with a polyolefin resin surface unless additive is present to prevent syneresis.

Organic surface-active agents may be used in the dental cream of the present invention to achieve increased prophylactic action, assist in achieving thorough and complete dispersion of the instant compositions throughout the oral cavity, and render the dental creams more cosmetically acceptable. The organic surface-active material may be anionic, nonionic, ampholytic or cationic in nature, but it is preferred to employ as the surfaceactive agent a detersive material which imparts to the composition detersive and foaming properties. Suitable types of such detergents are water-soluble salts of higher fatty acid monoglyceride monosulphates, such as the sodium salt of the monosulphated monoglyceride of hydrogenated coconut oil fatty acids, higher alkyl sulphates, such as sodium lauryl sulphate, alkylaryl sulphonates, such as sodium dodecyl benzene sulphonate, olefinsulphonates, such as sodium olefin sulphonate in which the olefin group contains 12–22 carbon atoms, higher alkyl sulphoacetates, higher fatty acid ester of 1,2-dihydroxy propane sulphonates, and the substantially saturated higher aliphatic acyl amides of lower aliphatic amino carboxylic acid compounds such as those having 12–16 carbon atoms in the fatty acid, alkyl or acyl radicals and the like. Examples of the last mentioned amides are N-lauroyl sarcosine, and the sodium, potassium, and ethanolamine salts of N-lauroyl, N-myristoyl or N-palmitoyl sarcosine, which should be substantially free from soap or similar higher fatty acid material which tends to substantially reduce the effect of these compounds in compositions of the present invention. The amides are particularly advantageous since they exhibit a prolonged and marked effect in the inhibition of acid formulation in the oral cavity due to carbohydrates breakdown in addition to exerting some reduction in the solubility of tooth enamel in acid solutions. Another desirable material is a long chain fatty acid sodium monoglyceride sulphonate used alone or in combination with sodium lauryl sulphate.

Other particularly suitable surface-active materials include nonionic agents such as condensates of sorbitan monostearate with approximately 20 moles of ethylene oxide, condensate of ethylene oxide with propylene glycol ("Pluronic" materials) and amphoteric agents such as long chain (alkyl) amino-alkylene alkylated amine derivatives, which are available under the trademark "Miranol" such as Miranol C₂M. Cationic surface-active germicides and antibacterial compounds such as di-isobutyl phenoxy ethoxy ethyl dimethyl benzyl ammonium chloride, benzyl dimethyl stearyl ammonium chloride, benzyl diethyl stearyl ammonium chloride, tertiary amines having one fatty alkyl group (of from 12–18 carbon atoms) and two (poly) oxyethylene groups attached to the nitrogen (typically containing a total of from about 2 to 50 ethanoxy groups per molecule) and salts thereof with acids, and compounds of the structure

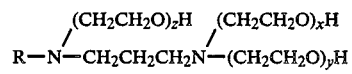

where R is a fatty alkyl group containing from about 12 to 18 carbon atoms, and x, y and z total 3 or higher, as well as salts thereof with mineral or organic acids, may also be used. It is preferred to use from about 0.05 to 5% by weight of the foregoing surface-active materials in the dental cream. It is most preferred that the surface-active agent be an anionic material, particularly sodium lauryl sulphate.

The dental cream suitably may also contain a fluorine-containing compound having a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride (SnF₂.KF), sodium hexafluorostannate, stannous chlorofluoride, sodium fluorozirconate, and sodium monofluorophosphate. These materials which disassociate or release fluorine-containing ions in water, suitably may be present in an effective but nontoxic amount, usually within the range of about 0.01 to 1% by weight of the water soluble fluorine content thereof.

The preferred fluorine-containing compound is sodium monofluorophosphate typically present in an amount of about 0.076 to 7.6% by weight, preferably 0.76%. A mixture of sodium monofluorophosphate and sodium fluoride is also desirable, for instance in a weight ratio of about 2:1 based on fluoride.

Any suitable flavoring or sweetening materials may be employed in formulating a flavor for the composition of the present invention. Examples of suitable flavoring constituents include the flavoring oils. e.g., oils of spearmint, peppermint, wintergreen, sassafras, clove, sage, eucalyptus, marjoram, cinnamon, lemon and orange, as well as methyl salicylate. Suitable sweetening agents include sucrose, lactose, maltose, xylitol, sodium 6-methyl-3,4-dihydro-1,2,3-oxathiazine-4-one, sodium cyclamate, perillartine and sodium saccharin. Suitably, flavor and sweetening agents may together comprise from about 0.01 to 5% or more of the compositions of the instant invention.

Various other materials may be incorporated in the dental cream. Examples thereof are coloring or whitening agents or dyestuffs, anti-corrosive agents, silicones, chlorophylic compounds, ammoniated materials such as urea, diammonium phosphate and mixtures thereof and other constituents. Whitening agents, such as titanium dioxide, typically in amounts of about 0.5–2%, may be beneficial to the appearance of the dental composition, since upon aging, some discoloration may occur.

The adjuvants are incorporated in the instant compositions in amounts which do not substantially adversely affect the properties and characteristics desired and are selected and used in proper amounts depending upon the particular type of composition involved.

Antibacterial agents may also be employed in the oral compositions of the instant invention in an amount of about 0.01–5% by weight. Typical antibacterial agents include:

$N^1$-(4-chlorobenzyl)-$N^5$-(2,4-dichlorobenzyl) biguanide;
p-chlorophenyl biguanide;
4-chlorobenzyhydryl biguanide;
4-chlorobenzhydrylguanylurea;
N-3-lauroxypropyl-$N^5$-chlorobenzylbiguanide;
1,6-di-chlorophenylbiguanidohexane;
1,6-bis-(2-ethylhexylbiguanide) hexane;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine and their non-toxic acid addition salts.

The package into which the dental cream is incorporated may be any polyolefin laminate dental cream tube. For instance, the tube may be as elementary as is described in U.S. Pat. No. 3,260,410 to Brandt et al, the disclosure of which is incorporated herein by reference. As described in the example thereof, an aluminum foil base having a thickness of about 0.0013 cm was heated to a temperature of approximately 177° C., and one face of the heated foil was contacted by an extrudable film of a random copolymer of ethylene and acrylic acid (acid content 3±0.5% and melt index 8±1), while the opposite surface thereof had placed thereagainst a film of low density polyethylene.

Using driven rolls a laminated base was obtained in which the copolymer layer was about 6 mils and the polyethylene layer was approximately 5 mils in thickness. The base was then shaped into tubular form and sealed.

After severing the tubular form into tube bodies, the tubes can be packed with the dental cream of the present invention.

Polyolefin laminate dentifrice tubes containing more intermediate layers may also be successfully used with the dental cream of the present invention without undergoing syneresis. For instance, the multiple layer flexible sheet structure for dental cream tubes described as "Prior Art" in U.S. Pat. No. 4,418,841 to Eckstein may be employed as well as the more crack resistant structures described therein. The disclosure of U.S. Pat. No. 4,418,841 to Eckstein is incorporated herein by reference. In fact, dental creams of the present invention packed in tubes of sheet material identified as Prior Art A and A-1 in U.S. Pat. No. 4,418,841 are very satisfactory and undergo substantially no syneresis. Such tubes A and A-1 are comprised of layers as set forth below, in the order of outermostlayer to innermost layer.

| A | A-1 |
|---|---|
| 1.5 mil LDPE | 1.5 mil LDPE |
| 2.0 mil Pigmented LDPE | 2.0 mil Pigmented LDPE |
| 1.6 mil Paper | 1.6 mil Paper |
| 0.7 mil LDPE | 2.0 mil LDPE |
| 3.3 mil EAA | 1.0 mil OPP |
| 0.7 mil Foil | 1.0 mil EAA |
| 2.0 mil EAA | 0.7 mil Foil |
| 1.2 mil LDPE | 2.0 mil EAA |
| 13.0 mil Total | 1.2 mil LDPE |
| | 13.0 mil Total |

In A and A-1 the abbreviations have the following meanings:
LDPE: low density polyethylene
EAA: ethylene acrylic acid
OPP: oriented polypropylene Mechanically operated dispensers, such as the dispenser for, in particular, pasty substances, described in U.S. Pat. No. 4,437,591 to von Schuckmann, the disclosure of which is incorporated herein by reference, may also be used with the practice of the present invention. The housing of such dispensers is commonly composed of a polyolefin resin such as polypropylene. Thus the housing resin is in essence a layer, the inner surface of which is in contact with dental cream. When the dental cream of the present invention is packaged in such a polypropylene mechanical dispenser, it undergoes substantially no syneresis.

The advantages of the invention are also present when the dental cream is packed in a flexible sachet having a polyolefin surface, typically of low density or medium density polyethylene.

The following illustrative examples are further illustrative of the nature of the present invention but it is understood that the invention is not limited thereto. All amounts and proportions are by weight except as otherwise indicated.

EXAMPLE 1

The following dental creams are prepared to creamy consistencies and packed into tubes of each of laminated structures A and A-1, set forth above:

| | Parts | | | |
|---|---|---|---|---|
| | 1 | 2 | 3 | 4 |
| Glycerine | 8.000 | 8.000 | 8.000 | 8.000 |
| Sorbitol (70%) | 16.000 | 15.000 | 15.500 | 14.000 |
| Sodium Carboxymethyl cellulose | 1.000 | 1.000 | 1.000 | 1.000 |
| Sodium Saccharin | 0.200 | 0.200 | 0.200 | 0.200 |
| Sodium Monofluorophosphate | 0.760 | 0.760 | 0.760 | 0.760 |
| Sodium Diacid Orthophosphate monohydrate | 0.250 | 0.250 | 0.250 | 0.250 |
| Deionized water-irradiated | 19.700 | 19.700 | 19.700 | 19.700 |
| Alpha-alumina trihydrate (C-333) | 52.000 | 52.000 | 52.000 | 52.000 |
| Sodium lauryl sulfate | 1.200 | 1.200 | 1.200 | 1.200 |
| Flavor | 0.890 | 0.890 | 0.890 | 0.890 |
| Polyethylene Glycol Average M.W. 600 | — | 1.000 | 0.500 | 2.000 |
| pH | 7.0 | 7.0 | 7.0 | 7.1 |

After aging for at least 13 weeks at 25° C., dental creams (2), (3) and (4) remain creamy in consistency in laminate tubes of each of laminate Structures A and A-1, while dental cream (1) separates into liquid and solid phases within 1 week at 25° C. in both of tubes of Structures A and A-1.

EXAMPLE 2

Dental creams (1) to (4) are incorporated into a mechanical dispenser in accordance with U.S. Pat. No. 4,437,591 composed of polypropylene housing. Dental creams (2), (3) and (4) retain their creamy consistency while dentifice (1) separates into liquid and solid phases.

EXAMPLE 3

Similar results to those described above for Examples 1 and 2 are observed when:
(i) the relative amounts of glycerine, sorbitol (70%) and polyethylene glycol—av. m.w. 600 are: 6:24:2 vs. 6:24:0 and 18:6:2 vs. 18:6:0;
(ii) polyethylene glycol—av. m. wts. 200 and 1000 are used in place of polyethylene glycol—av. m.w. 600;
(iii) The dental creams are packed in laminated tubes in accordance with U.S. Pat. No. 3,260,410;
(iv) The dental creams are packed in crack-resistant laminated tubes in accordance with U.S. Pat. No. 4,418,841;
(v) The dental creams are packed in flexible sachets of the following structure from outermost to innermost layer:
12.2μ polyethylene terephthalate
21.3μ white ethylene acrylic acid
9.0μ foil
3.3μ ethylene acrylic acid
25.4μ medium density polyethylene;
(vi) Mixture of 0.3 parts of sodium carboxymethylcellulose and 0.6 parts of xanthan replace of sodium carboxymethyl cellulose as the sole gelling material;
(vii) 3.000 parts of calcined alumina replace 3.000 parts of alpha-alumina trihydrate; and
(viii) 10 parts of insoluble sodium metaphosphate replace 10.000 parts of alpha-alumina trihydrate.
(ix) sodium cyclamate replaces sodium saccharin It is understood that the foregoing detailed description is given merely by way of illustration and that variations may be made therein without department from the spirit of the invention.

I claim:

1. A packaged dental cream herein said dental cream is in direct contact with a low or medium density polyethylene or polypropylene surface, wherein syneresis occurs in said dental cream due to said direct contact when said dental cream comprises as ingredients an aqueous vehicle comprising a liquid vehicle comprising about 10-50% by weight of water and glycerine and sorbitol together in amount of about 15-50% by weight, the weight ratio of glycerine to sorbitol being from about 0.25:1 to about 3:1, a dental cream solid vehicle comprising about 0.05-10% by weight of a dental cream gelling agent and about 20-75% by weight of a dentally acceptable water-insoluble polishing material at least 50% by weight of which is alpha-alumina trihydrate, and a water-soluble inorganic phosphate compound in amount which reduces the pH of the dental cream to about 6-8; said dental cream comprising said ingredients and as an additive which prevents syneresis in said dental cream upon said direct contact about 0.5-2% by weight of polyethylene glycol of average moelecular weight of about 200-1000, the weight ratio of the total amount of glycerine and sorbitol to said polyethylene glycol being from about 60:1 to about 6:1.

2. The packaged dental cream claimed in claim 1 wherein the weight ratio of glycerine to sorbitol is from about 0.25:1 to about 0.8:1 and the weight ratio of the total amount of glycerine and sorbitol to said polyethylene glycol is from about 15:1 to about 10:1.

3. The packaged dental cream claimed in claim 2 wherein the weight ratio of glycerine to sorbitol is from about 0.6:1 to about 0.8:1.

4. The packaged dental cream claimed in claim 1 wherein the average molecular weight of said polyethylene glycol is about 600-1000.

5. The packaged dental cream claimed in claim 4 wherein the average molecular weight of said polyethylene glycol is about 600.

6. The packaged dental cream claimed in claim 1 wherein said alpha-alumina trihydrate is the sole polishing agent present.

7. The packaged dental cream claimed in claim 1 wherein said inorganic compound which reduces the pH is an orthophosphate.

8. The packaged dental cream claimed in claim 7 wherein said compound containing orthophosphate ion is selected from the group consisting of orthophosphoric acid, alkali metal diacid orthophosphate, ammonium diacid orthophosphate, alkali metal monoacid orthophosphate and ammonium monacid orthophosphate.

9. The packaged material claimed in claim 8 wherein said material containing orthophosphate ion is a sodium diacid ortho-phosphate.

10. The packaged material claimed in claim 9 wherein said sodium diacid orthophosphate is sodium diacid orthophosphate monohydrate.

11. The packaged dental cream claimed in claim 1 wherein said dental cream is packaged in direct contact with low or medium density polyethylene.

12. The packaged dental cream claimed in claim 1 wherein said dental cream is packaged in direct contact with said polypropylene.

* * * * *